United States Patent [19]

Kees, Jr. et al.

[11] Patent Number: 4,777,939
[45] Date of Patent: Oct. 18, 1988

[54] RETRACTOR STRUCTURE

[75] Inventors: George Kees, Jr., Alexandria, Ky.; Set Shahbabian, Cincinnati; Horst R. Hickmann, Anderson Township, Hamilton County, both of Ohio

[73] Assignee: George Kees Research & Development Co., Inc., Wilder, Ky.

[21] Appl. No.: 473,531

[22] Filed: Mar. 9, 1983

[51] Int. Cl.[4] ............................................. A61B 17/02
[52] U.S. Cl. ..................................................... 128/20
[58] Field of Search ......................................... 128/4–8, 128/20, 200.26, 753, 754, 92 EA, 305.3, 303.11, 329 R, 341

[56] References Cited

U.S. PATENT DOCUMENTS

| 1,798,124 | 3/1931 | Hunn | 128/20 |
| 1,928,893 | 10/1933 | Hoard | 128/341 |
| 2,238,563 | 4/1941 | Jacques | 128/341 |
| 3,542,015 | 11/1970 | Steinman | 128/20 |
| 3,750,652 | 8/1973 | Sherwin | 128/20 |
| 3,759,263 | 9/1973 | Taylor | 128/305.3 |
| 3,989,033 | 11/1976 | Halpern et al. | 128/754 |
| 4,331,138 | 5/1982 | Jessen | 128/200.26 |
| 4,421,107 | 12/1983 | Esks et al. | 128/20 |

Primary Examiner—Max Hindenburg
Attorney, Agent, or Firm—James W. Pearce; Roy F. Schaeperklaus

[57] ABSTRACT

A retractor which includes a body portion and a side arm portion extending transversely of the body portion. A first hook member is mounted on the body portion and a second hook member is mounted for movement on the body portion between a contracted position adjacent the first hook member and an extended position. The hook members have oppositely directed pivot point portions which engage opposed faces of adjacent vertebrae. The retractor pivots about the pivot point portions.

5 Claims, 6 Drawing Sheets

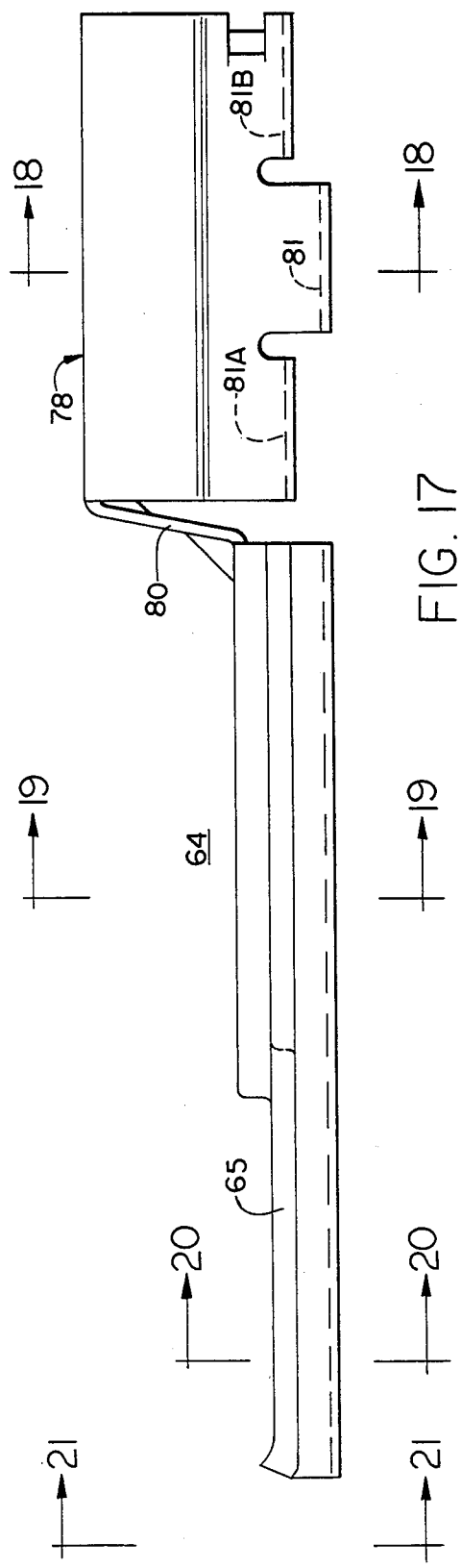
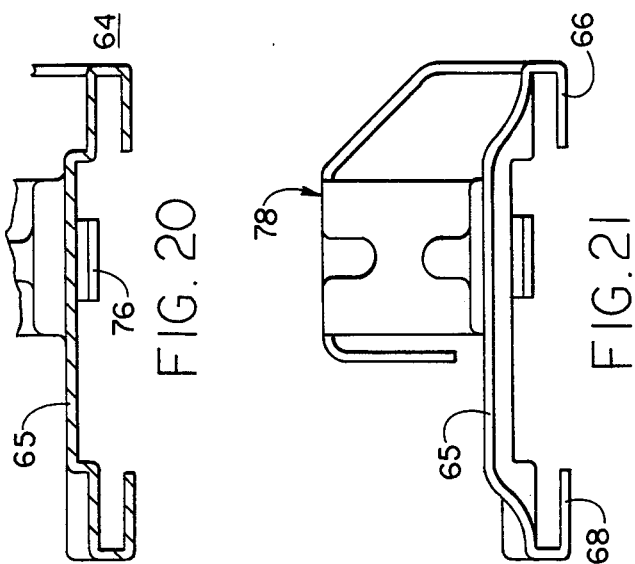
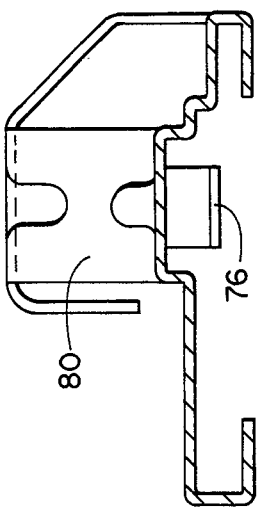
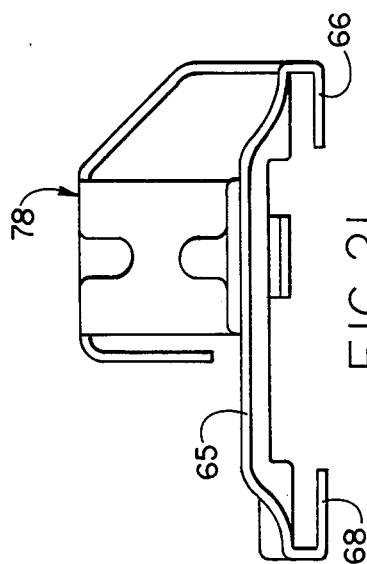

RETRACTOR STRUCTURE

This invention relates to a retractor structure. More particularly, this invention relates to a retractor which holds portions of a throat in retracted position during an operation.

An object of this invention is to provide a retractor which can be anchored on body portions of adjacent vertebrae and can pivot about anchor points to urge portions of the throat to retracted position.

A further object of this invention is to provide such a retractor which includes an adjustable weight which can urge the retractor in retracting direction with a selected force.

Briefly, this invention provides a retractor which includes a body that carries hook members which can be anchored on opposed faces of adjacent vertebrae. One of the hook members is anchored in the superior face of the body of one vertebra and the other hook member is anchored in the inferior face of the body of an adjacent vertebra. Spring means urges the hook members apart to firmly engage the body faces of the vertebrae. A hook operator is provided for urging the hook numbers together as the retractor body is inserted into an incision in the throat to one side of throat portions to be retracted. The retractor can pivot about point portions of the hook members, which engage the body faces. An elongated arm extends to one side of the body portion of the retractor, and a weight can be adjustably positioned on the elongated arm for urging the body portion of the retractor to retract the throat portions.

The above and other objects and features of the invention will be apparent to those skilled in the art to which this invention pertains from the following detailed description and the drawings, in which:

FIG. 17 is a view in side elevation of the shield;

FIG. 18 is a view in section taken on the line 18—18 in FIG. 17;

FIG. 19 is a view in section taken on the line 19—19 in FIG. 17;

FIG. 20 is a view in section taken on the line 20—20 in FIG. 17; and

FIG. 21 is a view in end elevation of the shield looking in the direction of the arrows 21—21 in FIG. 17;

In the following detailed description and the drawings, like reference characters indicate like parts.

Figure 1:
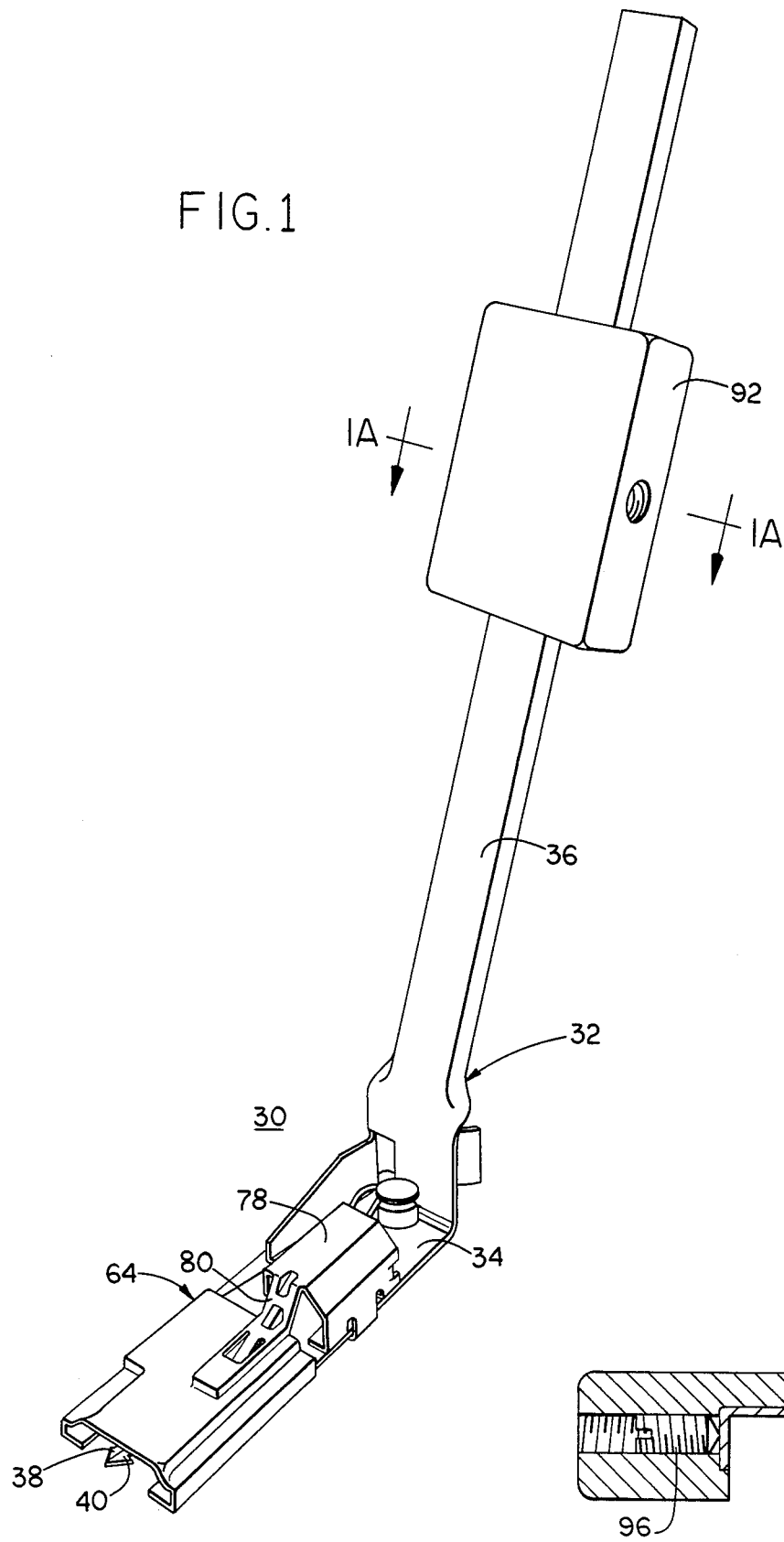
FIG. 1 is a perspective view of a retractor constructed in accordance with an embodiment of this invention.
Figure 1A:
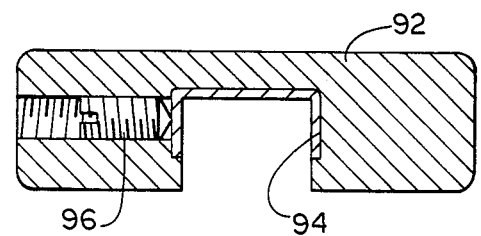
FIG. 1A is a view in section taken on the line 1A—1A in FIG. 1.
Figure 4:
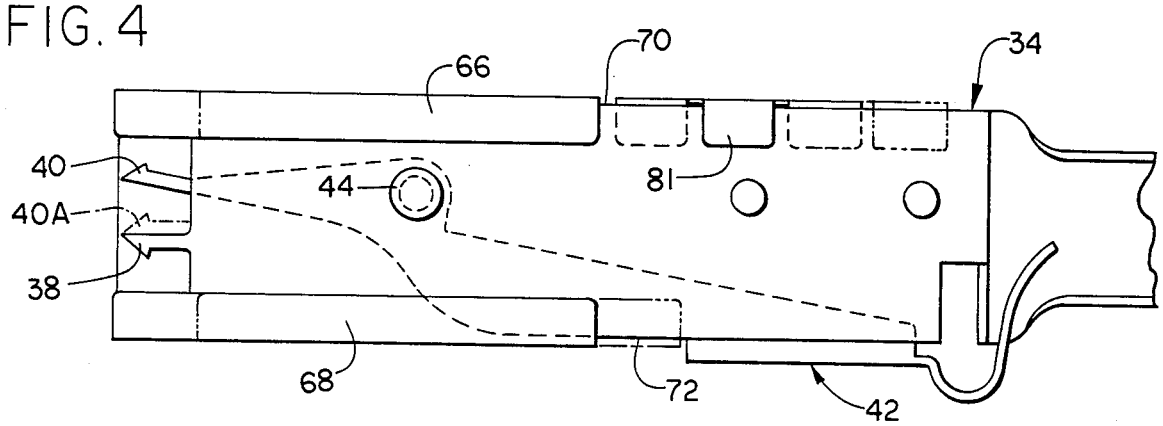
FIG. 4 is a fragmentary bottom plan view of the retractor body, a movable hook being shown in full lines in extended position, a contracted position of the movable hook being shown in dot-dash lines.
Figure 5:
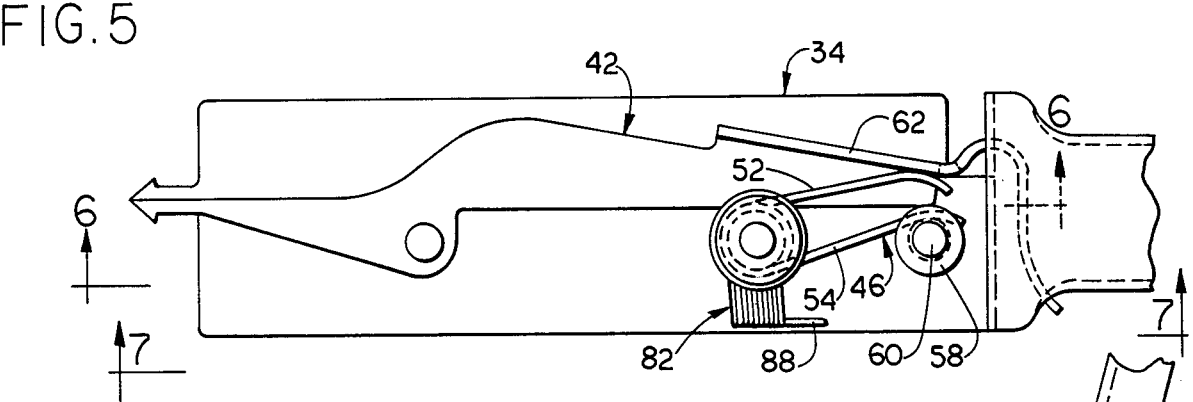
FIG. 5 is a fragmentary top plan view of the head portion with the shield removed, the movable hook being shown in contracted position.
Figure 6:
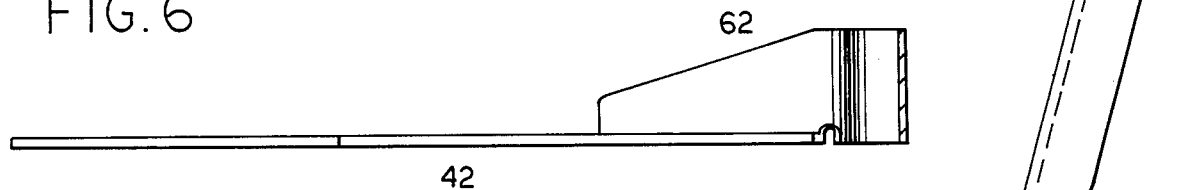
FIG. 6 is a view in section of a hook supporting member of the retractor taken on the line 6—6 in FIG. 5.
Figure 7:
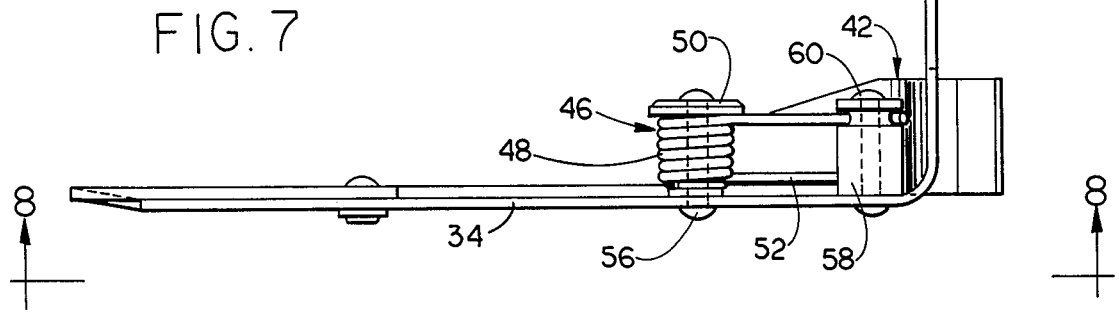
FIG. 7 is a view in side elevation of the retractor with the shield removed looking in the direction of the arrows 7—7 in FIG. 5.
Figure 8:
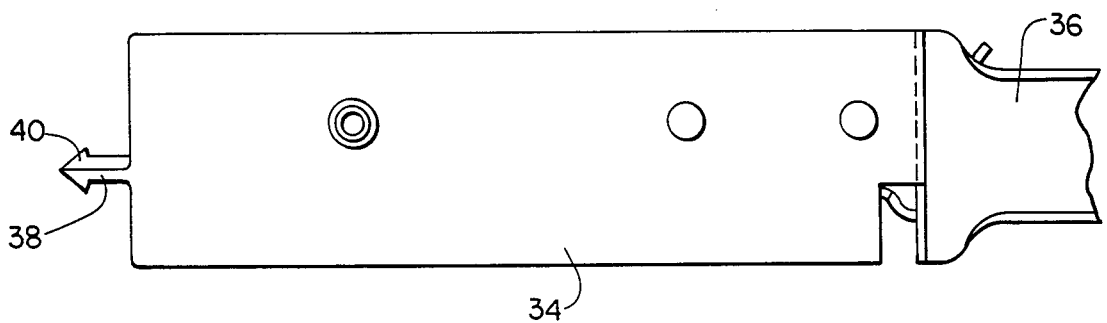
FIG. 8 is a bottom plan view of the retractor with the shield removed, the movable hook being shown in contracted position.
Figure 13:
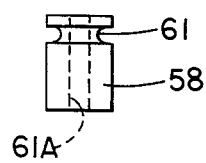
FIG. 13 is a view in side elevation of a spring holding member of the retractor.
Figure 14:
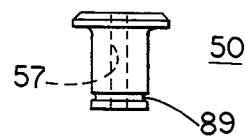
FIG. 14 is a view in side elevation of another spring holding member of the retractor.

In FIG. 1 is shown a retractor 30 constructed in accordance with an embodiment of this invention. The retractor 30 includes a main member 32 which includes a body portion 34 and a side arm portion 36. At one end of the body portion 34 is provided a hook member 38, as shown in FIG. 4. A second hook member 40 is carried by a hook support pivoting bar 42. The hook support pivoting bar 42 is pivotally mounted on the body portion 34 by a pivot member 44. The second hook member 40 and the hook support pivoting bar 42 can swing between a contracted position shown in FIG. 1 and in dot-dash lines at 40A in FIG. 4, and an extended position shown in full lines at 40 in FIG. 4. A spring 46 (FIGS. 5 and 7) urges the hook support pivoting bar 42 to hook extended position. The spring 46 includes a central helical portion 48 mounted on a spring support 50 and arms 52 and 54. The spring support 50 (FIG. 14) is mounted on the body portion 34 by means of a rivet 56, which extends through a central bore 57 in the spring support 50. The spring arm 54 engages a spring support 58 (FIG. 13). The spring support 58 is mounted on the body portion 34 by means of a rivet 60. The spring arm 54 is received in a slot 61 in the spring support 58. The rivet 60 extends through a central bore 61A in the spring support 58. The spring arm 52 engages a flange 62 of the hook support pivoting bar 42.

Figure 2:
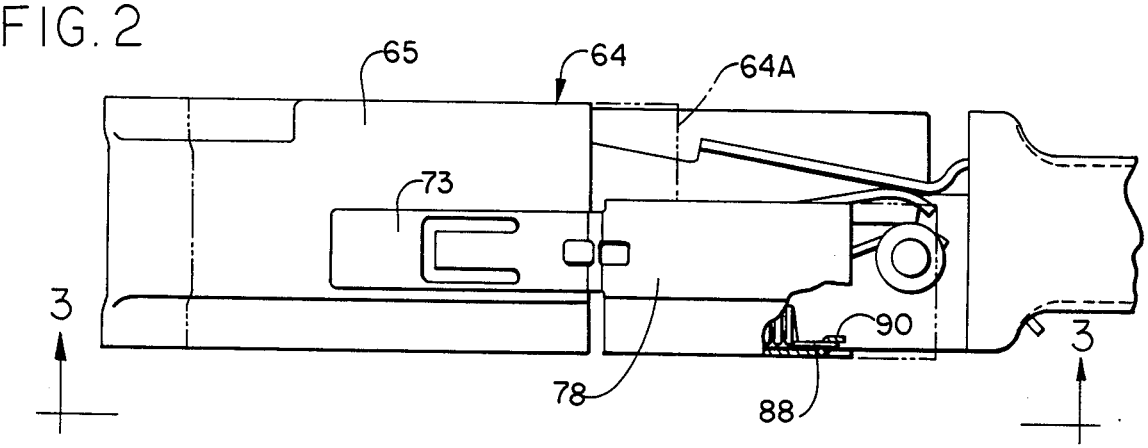
FIG. 2 is a fragmentary plan view of a head portion of the retractor, parts being broken away to reveal details of structure, a retracted position of a shield being shown in double dot-dash lines.
Figure 3:
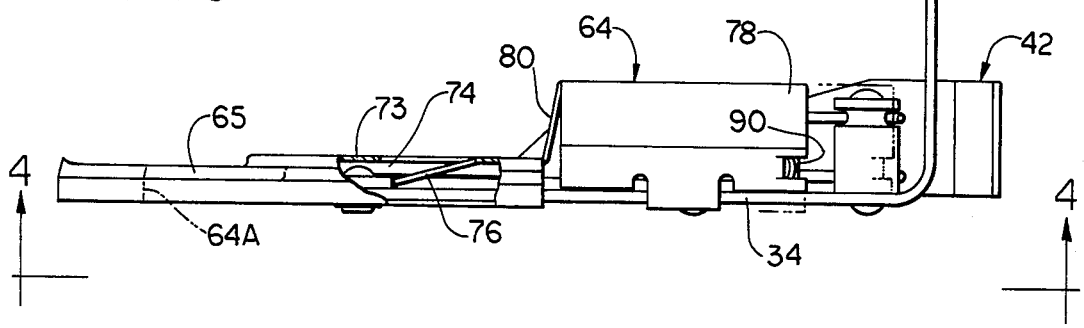
FIG. 3 is a fragmentary view in side elevation of the head portion of the retractor looking in the direction of the arrows 3—3 in FIG. 2.
Figure 15:
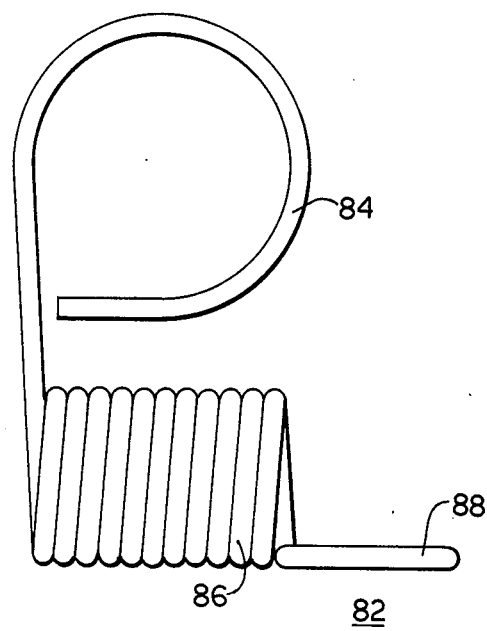
FIG. 15 is an enlarged plan view of a spring of the retractor.
Figure 16:
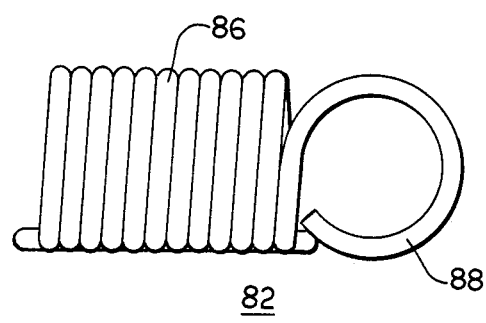
FIG. 16 is a view in side elevation of the spring shown in FIG. 15.

A shield 64 is slideably mounted on the body portion 34. The shield 64 includes a guide portion 65 provided with return bend portions 66 and 68. The return bend portions 66 and 68 extend around opposite lengthwise edges 70 and 72, respectively, of the body portion 34. A central portion 73 of the guide portion 65 is deformed away from the return bend portions 66 and 68 to form a space 74 for the hook support pivoting bar 42. A stop flange 76 is bent from the central portion 73 for engagement with the hook support pivoting bar 42 to limit sliding of the shield 64 at the position shown in full lines in FIG. 3. When the shield 64 is in the position shown in full lines in FIGS. 3 and 4, the hook members 38 and 40 are covered by the shield 64. A head member 78 of the shield 64 is connected to the guide portion 65 by a connector strip 80. The head member 78 includes a return bend flange 81 which runs on one side of the body portion 34 and return bend flanges 81A and 81B which slide on an opposite side of the body portion 34 to steady the head member 78. A tension spring 82 (FIGS. 15 and 16) includes an end loop 84 mounted on the spring support 50, a central helical portion 86, and a second end loop 88. The end loop 84 is received in a slot 89 of the spring support 50. The second end loop 88 is mounted on a tab 90 of the head member 78 to urge the shield to the full line position of FIG. 2. The shield 64 can be pushed against the force of the tension spring 82 to the double dot-dash line position shown at 64A in FIGS. 2 and 3 to reveal the hook members 38 and 40.

The side arm portion extends transversely of the body portion 34 at an angle of approximately 105° to a line 93 (FIG. 3) parallel to the body portion 34. A weight 92 is slideably mounted on the side arm portion 36. A slot 94 in the weight 92 receives the side arm portion 36. A set screw 96 can hold the weight at selected positions along the side arm portion 36.

Figure 11:
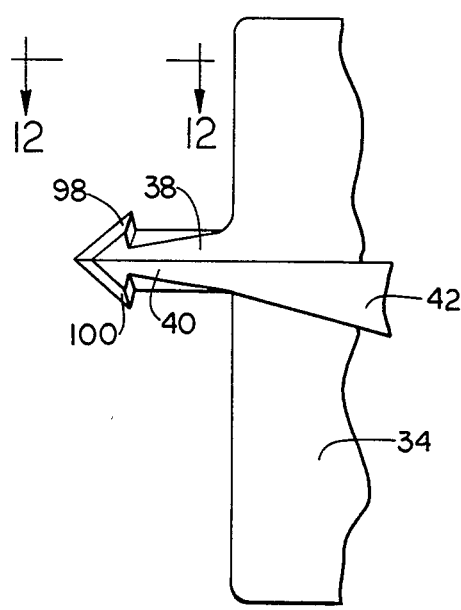
FIG. 11 is an enlarged fragmentary plan view showing details of construction of the hook members, the hook members being shown in contracted position.
Figure 12:
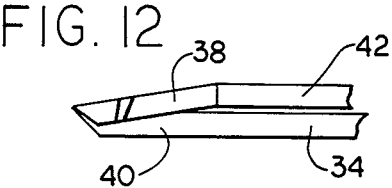
FIG. 12 is a view in side elevation looking in the direction of the arrows 12—12 in FIG. 11.

Details of construction of the hook members 38 and 40 are shown in FIGS. 11 and 12. The hook members 38 and 40 include oppositely and outwardly directed pivot point portions 98 and 100, respectively. The hook member 38 is bent at an angle of approximately 10 degrees to the body of the hook support pivoting bar 42, as shown in FIG. 12, to place the pivot point portions in substantial alignment.

Figure 9:
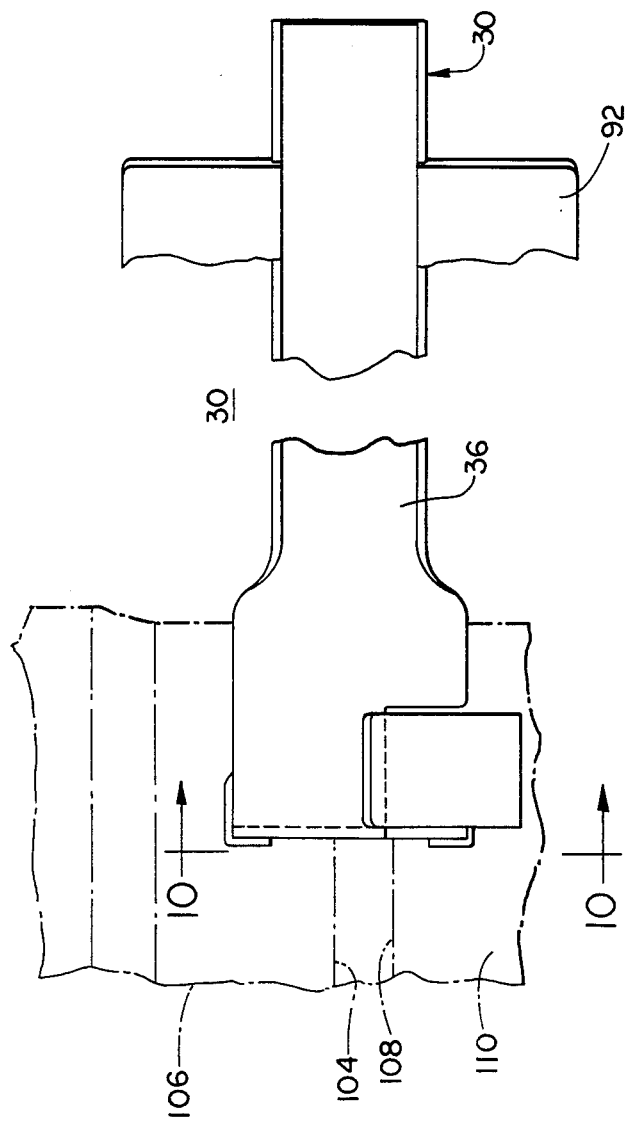
FIG. 9 is a view of the retractor body in end elevation, portions of three vertebrae and elements between vertebrae being shown in dot-dash lines in association therewith, a fragmentary portion of a side arm being shown in connection therewith.
Figure 10:
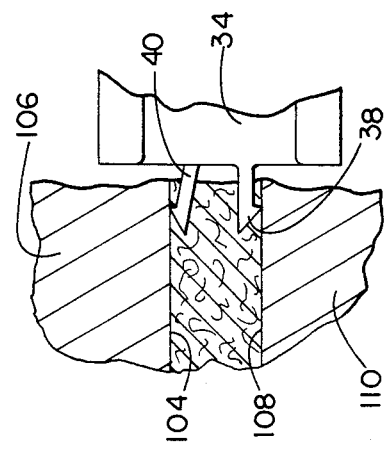
FIG. 10 is a fragmentary view in section taken on the line 10—10 in FIG. 9.

Use of the retractor 30 is illustrated in FIGS. 9 and 10. When an incision has been made in a throat of a patient (not shown in detail) to one side of throat elements to be retracted, the hook support pivoting bar 42 is swung to contracted position to bring the hook members into close proximity as shown in FIG. 1, and the body portion 34 is inserted into the incision to dispose the hook members between an inferior face 104 of a first vertebra 106 and a superior face 108 of an adjacent vertebra 110. As the body portion 34 is inserted, the shield 64 is pushed to the position shown at 64A in FIGS. 2 and 3 to expose the hook members 38 and 40. The hook support pivoting bar 42 is released, and the hook member 40 swings away from the hook member 38 under the influence of the spring 46 so that the pivot pin portions 98 and 100 of the hook members 38 and 40, respectively, become seated in the vertebrae faces 104 and 108, as shown in FIG. 10, and the weight 92 causes the side arm portion 36 of the retractor 30 to pivot downwardly and to the right as shown in FIG. 9 about the pivot pin portions so that the retractor 30 urges the throat portions to the right of the body portion 34 to the right with a pressure determined by the position of the weight 92 on the side arm portion 36.

The retractor illustrated in the drawings and described above is subject to structural modification without departing from the spirit and scope of the appended claims.

Having described our invention, what we claim as new and desire to secure by letters patent is:

1. A retractor which comprises a body portion, a side arm portion extending transversely of the body portion, a first hook member mounted on the body portion, a second hook member mounted for movement on the body portion between a contracted position adjacent the first hook member and an extended position, the hook members having oppositely directed pivot point portions, the pivot point portions of the hook members being spaced sufficiently to engage opposed faces of adjacent vertebrae when the second hook member is in the extended position, and means for urging the second hook member to extended position to cause the pivot point portions of the hook members to engage opposed faces of adjacent vertebrae, the retractor pivoting about the pivot point portions.

2. A retractor as in claim 1 which includes a weight slideably mounted on the side arm portion and means for locking the weight in selected position on the side arm portion.

3. A retractor as in claim 1 in which the second hook member is pivotally mounted on the body portion and in which the means for urging the second hook member to extended position includes spring means urging the second hook member to swing to extended position.

4. A retractor as in claim 1 which includes a shield slideably mounted on the body portion and slideable between a normal position overlying the hook members and an extended position free of the hook members.

5. A retractor as in claim 4 which includes spring means urging the shield to normal position.

* * * * *